US007084118B2

(12) United States Patent
Armstrong et al.

(10) Patent No.: US 7,084,118 B2
(45) Date of Patent: Aug. 1, 2006

(54) COMBINATION TREATMENT WITH T-PA VARIANT AND LOW MOLECULAR WEIGHT HEPARIN

(75) Inventors: Paul Armstrong, Edmonton (CA); Hal Barron, San Francisco, CA (US); Silvano Berioli, Perugia (IT); Frederique Bigonzi, 1'Hay les Roses (FR); Erich Bluhmki, Schwendi (DE); Richard Chin, San Francisco, CA (US); Christopher Granger, Durham, NC (US); Frans Van De Werf, Herent (BE); Fong Wang-Clow, Los Altos Hills, CA (US)

(73) Assignees: Genentech, Inc., South San Francisco, CA (US); Boehringer Ingelheim Pharmaceuticals, Inc., Ridgefield, CT (US); Aventis Pharma, S.A., Antony (FR); Boehringer Ingelheim Pharma KG, Ingelheim/Rhein (DE)

( * ) Notice: Subject to any disclaimer, the term of this patent is extended or adjusted under 35 U.S.C. 154(b) by 0 days.

(21) Appl. No.: 10/371,778

(22) Filed: Feb. 21, 2003

(65) Prior Publication Data

US 2004/0029798 A1    Feb. 12, 2004

Related U.S. Application Data

(60) Provisional application No. 60/359,327, filed on Feb. 22, 2002.

(51) Int. Cl.
   *A61K 38/00*    (2006.01)
   *C07K 1/00*     (2006.01)
   *C07K 14/00*    (2006.01)
   *C07K 17/00*    (2006.01)

(52) U.S. Cl. ........................ 514/12; 530/350
(58) Field of Classification Search ............ 424/94.64, 424/94.63; 435/172.3, 212, 215, 216, 219, 435/226; 514/12
See application file for complete search history.

(56) References Cited

U.S. PATENT DOCUMENTS

| | | | |
|---|---|---|---|
| 4,281,108 A | 7/1981 | Fussi | 536/21 |
| 4,687,765 A | 8/1987 | Vairel et al. | 514/56 |
| 4,766,075 A | 8/1988 | Goeddel et al. | 435/240.2 |
| 4,977,250 A | 12/1990 | Diaz et al. | 536/21 |
| 5,106,734 A | 4/1992 | Nielsen | 435/84 |
| 5,130,143 A | 7/1992 | Strickland et al. | 424/94.64 |
| 5,279,824 A | 1/1994 | Sawyer et al. | |
| 5,308,617 A | 5/1994 | Halluin | 424/94.64 |
| 5,389,618 A | 2/1995 | Debrie | 514/56 |
| 5,510,330 A | 4/1996 | Martin et al. | |
| 5,576,304 A | 11/1996 | Kakkar et al. | 514/56 |
| 5,612,029 A * | 3/1997 | Bennett et al. | 424/94.64 |
| 5,690,931 A * | 11/1997 | Martin et al. | 424/94.64 |
| 5,753,702 A | 5/1998 | Bednar et al. | 514/552 |
| 5,849,689 A | 12/1998 | Chamow et al. | 514/8 |
| 6,235,279 B1 | 5/2001 | Martin et al. | 424/94.63 |

FOREIGN PATENT DOCUMENTS

| | | |
|---|---|---|
| EP | 0238304 A2 | 9/1987 |
| EP | 0238304 B1 | 9/1987 |
| EP | 0 372 969 | 6/1990 |
| EP | 0 643 772 B1 | 7/1997 |
| WO | WO 89/04368 | 5/1989 |
| WO | WO 95/26202 | 10/1995 |
| WO | WO 00/53168 | 9/2000 |

OTHER PUBLICATIONS

Single-bolus tenecteplase compared with front-loaded alteplase in acute myocardial infarction: the ASSENT-2 double-blind randomised trial. Assessment of the Safety and Efficacy of a New Thrombolytic Investigators. Lancet. Aug. 28, 1999;354(9180):716-22.*
Efficacy and safety of tenecteplase in combination with enoxaparin, abciximab, or unfractionated heparin: the ASSENT-3 randomised trial in acute myocardial infarction. □□Lancet. Aug. 25, 2001;358(9282):605-13.*
Rebello et al. Superiority of Enoxaparin over Heparin in combination with a GPOOb/IIa receptor antagonist during coronary thrombolysis in dogs, 2001, Thrombosis, V. 102, pp. 261-271.*
Goodman et al., Randomized trial of low molecular weight heparin (enoxaparin) versus unfractionated heparin for unstable coronary artery disease: one-year results of . . . , J Am Coll Cardiol. Sep. 2000;36(3):693-8.*
Cannon, Christopher et al., "TNK-Tissue Plasminogen Activator Compared With Front-Loaded Alteplase in Acute Myocardial Infarction" CIRCULATION 1998; 98 pp. 2805-2814.
Cannon, Christopher et al., "TNK-Tissue Plasminogen Activator in Acute Myocardial Infarction" CIRCULATION, 1997; 95 351-356.
Kawai, Chuichi et al., "A Prospective, Randomized, Double-Blind Multicenter Trial of a Single Bolus Injection of the Novel Modified t-PA E6010 in the Treatment of Acute Myocardial Infarction: Comparison With Native t-PA" JACC v29, No. 7, Jun. 1997, pp. 1447-1453.

(Continued)

*Primary Examiner*—Jon Weber
*Assistant Examiner*—Robert B. Mondesi
(74) *Attorney, Agent, or Firm*—Janet E. Hasak; Ginger R. Dreger; Heller Ehrman (57) ABSTRACT

The invention concerns an improved therapeutic regimen for the treatment of thrombolytic disorders, such as acute myocardial infarction (AMI). In particular, the present invention concerns the treatment of thrombolytic disorders, e.g. AMI, with a combination of a tissue plasminogen activator (t-PA) variant having improved fibrin specificity and extended plasma half-life when compared with wild-type human t-PA and a low molecular weight heparin.

40 Claims, 5 Drawing Sheets

OTHER PUBLICATIONS

Kawasaki, Tomihisa et al., "Thrombolytic Activity of YM866, a Novel Modified Tissue-Type Plasminogen Activator, in a Rabbit Model of Jugular Vein Thrombosis" Drug Development Research 33:33-38 (1994).

Saito, Yoshimasa et al., "Production and Characterization of a Novel Tissue-Type Plasminogen Activator Derivative in *Escherichia coli*" Biotechnol, Prog. v10, pp. 472-479 (1994).

Schweiger, Marc et al., "Early Coronary Intervention Following Pharmacologic Therapy for Acute Myocardial Infarction" The American Journal of Cardiology, v88 Oct. 2001 pp. 831-836.

Tanswell, Paul et al., "Pharmacokinetics and Fibrin Specificity of Alteplase During Accelerated Infusions in Acute Myocardial Infarction" JACC v19, No. 5, Apr. 1992 pp. 1071-1075.

van de Werf, Frans et al., "Safety assessment of single-bolus administration of TNK tissue-plasminogen activator in acute myocardial infarction: The ASSENT-1 trial" American Heart Journal, v137 No. 5, May 1999.

"Intravenous NPA for the treatment of infracting myocardium early" European Heart Journal, 21, 2005-2013 (2000).

"Efficacy and safety of tenecteplase in combination with enoxaparin, abciximab, or unfractionated heparin: the ASSENT-3 randomised trial in acute myocardial infarction" The Lancet, v358 Aug. 25, 2001 pp. 605-613.

"Single-bolus tenecteplase compared with front-loaded alteplase in acute myocardial infarction: the ASSENT-2 double-blind randomized trial" The Lancet, v354 Aug. 28, 1999, pp. 716-722.

Rawles, J., "Magnitude of benefit from earlier thrombolytic treatment in acute myocardial infarction: new evidence from Grampian region anistreplase trial (GREAT)", *BMJ*, 312,:212-215 (1996).

"TI In ASSENT-3 wird das Fibrinolytikum TNK-tPA geprueft", *SO Aerzte-Zeitung* 0-81,(062) (Apr. 2000) (translation).

"ASSENT 3 Trial Shows Heart Attack Patients May Benefit From New Treatment Regimen: Clot-Buster Plus Low-Molecular-Weight Heparin" Genentech press release Aug. 8, 2001.

"ASSENT-3: implication for future trial design and clinical practice", *European Heart Journal*, 23:911-912 (2002).

Hopfner, R, "Lanoteplase Genetics Institute"*Current Opinion in Investigational Drug*, 1(4):468-475, (Dec. 2000).

Nordt, T. et al., "Pharmacokinetics and Pharmacodynamics of Lanoteplase (n-PA)", *Thromb Haemost*, 82 (Suppl.):121-123 (1999).

Verstraete, M., "Newer Thrombolytic Agents", *Annals of Academy of Medicine* Singapore 28:424-433 (1999).

den Heijer, P. et al., "Evaluation of a Weight-Adjusted Single-Bolus Plasminogen Activator in Patients With Myocardial Infarction", *Circulation* 98:2117-2125 (1998).

Jang, I. et al., "A Multicenter, Randomized Study of Argatroban Versus Heparin as Adjunct to Tissue Plasminogen Activator (TPA) in Acute Myocardial Infarction: Myocardial Infarction With Novastan and TPA (MINT) Study", *Journal of the American College of Cardiology* 33(7):1879-1885 (1999).

Ross, A. et al., "Randomized Comparison of Enoxaparin, a Low-Molecular-Weight Heparin, With Unfractionated Heparin Adjunctive to Recombinant Tissue Plasminogen Activator Thrombolysis and Aspirin", *Circulation*, 104 :648-652 (2001).

Antman, E., "Hirudin in Acute Myocardial Infarction Safety Report from the Thrombolysis and Thrombin Inhibition in Myocardial Infaction (TIMI) 9A Trial", *Circulation* 90(4):1624-1630 (1994).

Antman, E., "Enoxaparin for the Acute and Chronic Management of Unstable Angina", Supplement I 504 to Circulation 98(17) No. 2649 (1998).

Braunwald, E. "Myocardial Reperfusion, Limitation of Infarct Size, Reduction of Left Ventricular Dysfunction, and Improved Survival", *Circulation* 79(2):441-444 (1989).

Braunwald, E., "The Open Artery Theory is Alive and Well Again", *NEJM* 329(22):1650-1652 (1993).

Cannon, C. et al., "GUSTO, TIMI and the case for Rapid Reperfusion" *Acta Cardiologica* 49:1-8 (1994).

Cannon C. et al., "Comparison of Front-Loaded Recombinant Tissue-Type Plasminogen Activator, Anistreplase and Combination Thrombolytic Therapy for Acute Myocardial Infarction: Results of the Thrombolysis in Myocardial Infarction (TIMI) Trial 4", *JACC* 24(7):1602-1610 (1994).

Cohen, M. et al., "A Comparison of Low-Molecular-Weight Heparin with Unfractionated Heparin for Unstable Coronary Artery Disease", *NEJM* 37(7):447-452 (1997).

Giugliano, R. et al., "Lower-dose heparin with fibrinolysis is associated with lower rates of intracranial hemorrhage", *Am. Heart J.* 141(5):742-750 (2001).

GUSTO IIb Investigators "A Comparison of Recombinant Hirudin with Heparin for the Treatment of Acute Coronary Syndromes" *NEJM* 335(11):775-782 (1996).

GUSTO Angiographic Investigators "The Effects of Tissue Plasminogen Activator, Streptokinase, or Both on Coronary-Artery Patency, Ventricular Function, and Survival After Acute Myocardial Infarction", *NEJM* 329(22):1615-1622 (1993).

GUSTO Investigators "An International Randomized Trial Comparing Four Thrombolytic Strategies For Acute Myocardial Infarction", *NEJM* 329(10):673-682 (1993).

GUSTO IIa Investigators "Randomized Trial of Intravenous Heparin Versus Recombinant Hirudin for Acute Coronary Syndromes", *Circulation* 90:1631-1637 (1994).

ISIS-3 "IDIS-3 a randomized comparison of streptokinase vs tissue plasminogen activator vs antistreplase and of aspirin plus heparin vs aspirin alone among 41 299 cases of suspected acute myocardial infarction", *The Lancet* 339(8796):753-770 (1992).

Umemura, K. "Thrombolytic efficacy of a modified tissue-type plasminogen activator, SUN9216, in the rat middle cerebral artery thrombosis model", *European J. of Pharma.* 262:27-31 (1994).

Linderer, T. et al., "Prehospital Thrombolysis: Beneficial Effects of Very Early Treatment on Infarct Size and Left Ventricular Function", *JACC* 22(5):1304-1310 (1993).

Schafer, A. "Low-Molecular-Weight Heparin for Venous Thromboembolism" *Hospital Practice* Jan. 15, 1997 pp. 99-106.

Weaver, W. et al., "Prehospital-Initiated vs Hospital-Initiated Thrombolytic Therapy" *JAMA* 270(10):1211-1216 (1993).

* cited by examiner

Figure 1: Trial profile

Figure 2: Kaplan-Meier curves for primary efficacy endpoint

Figure 3: Kaplan-Meier curves for primary efficacy plus safety endpoint

Figure 4: Relative risks and 95% CIs for primary efficacy composite endpoint in total study population and in prespecified subgroups Figure 5: Relative risks and 95% CIs for primary efficacy plus safety composite endpoint in total study population and in prespecified subgroups

COMBINATION TREATMENT WITH T-PA VARIANT AND LOW MOLECULAR WEIGHT HEPARIN

CROSS-REFERENCE TO RELATED APPLICATIONS

The present application is related to U.S. Provisional Application No. 60/359,327, filed Feb. 22, 2002, from which priority is claimed under 35 U.S.C. § 119(e), and which is hereby incorporated by reference in its entirety.

BACKGROUND OF THE INVENTION

1. Field of the Invention

The present invention concerns an improved therapeutic regimen for the treatment of thrombolytic disorders, such as acute myocardial infarction (AMI). In particular, the present invention concerns the treatment of thrombolytic disorders, e.g. AMI with a combination of a tissue plaminogen activator (t-PA) variant having improved fibrin specificity and extended plasma half-life (when compared with wild-type human t-PA) and an anti-thrombin agent having anti-Xa and/or anti-IIa activity, such as a low molecular weight heparin.

2. Description of the Related Art

Thrombolytic therapy has been a major advance in the treatment of acute myocardial infarction (AMI). Thrombolytics can re-establish perfusion in occluded arteries, resulting in smaller infarct size, improved left ventricular function, and improved short and long-term survival. See e.g., Braunwald E., *Circulation* 79:441–1 (1989); Braunwald, *N. Engl. J. Med.* 329:1650–2 (1993); *The GUSTO investigators. An international randomized trial comparing four thrombolytica strategies for acute myocardial infarction. N. Engl. J. Med.* 329:673–82 (1993).

However, current regimens of thrombolytic-antithrombic therapy continue to be limited by failure of initial recanalization and reocclusion in about 40–45% of patients (Cannon et al., *J. Am. Col. Cardiol.* 24:1602–10 (1994); The GUSTO Angiographic Investigators, *N. Engl. J. Med.* 329:1615–22 (1993); Cannon and Braunwald, *Acta Cardiol.* 49:1–8 (1994)). In addition, intracranial hemorrhage can occur in over 0.9% of the patients treated with thrombolytics (ISIS-3 (Third International study of Infarct Survival) Collaborative Group, *Lancet* 339:753–70 (1992); *The Global Use of Strategies to Open Occluded Coronary Arteries (GUSTO) IIb Investigators, N. Eng. J. Med.* 335:775–82 (1996); ASSENT-II Investigators, *Lancet* 354:716–22 (1999)).

Attempts to increase the efficacy of thrombolytic therapy by increasing the dose of thrombolytic have been unsuccessful because of unacceptably high incidence of intracranial hemorrhage. Also, an important factor in reducing mortality associated with AMI is the reduction of time to reperfusion (Rawles, J., *BMJ* 312:212–15 (1996); Linderer et al., *J. Am. Coll. Cardiol.* 22:212–215 (1996); Weaver et al., *JAMA* 270:1211–16 (1993)). Guidelines concerning the treatment of AMI have suggested a target figure of 90 minutes for the maximum delay between the patient seeing help and receiving thrombolysis. Despite encouraging results, pre-hospital thrombolysis has not been widely implemented, and the delay from symptom onset to arrival to hospital, which constitutes about two thirds of the overall delay, remains a major impediment to optimal reperfusion. Accordingly, there is a great need for a thrombolytic regimen that allows early intervention, provides high efficacy, and carries low risk of bleeding side-effects.

A particularly successful t-PA variant is tenecteplase (TNKase™), a t-PA variant with extended half-life and improved fibrin specificity when compared to native human t-PA. TNKase™ (TNK-t-PA; T103N, N117Q, KHRR (296–299)AAAA t-PA) is a 527 amino acids long glycoprotein developed by Genentech, Inc., which obtained FDA approval on Jun. 2, 2000 for use in the reduction of mortality associated with acute myocardial infarction (AMI). TNKase™ (tenecteplase) is a derivative of wild-type human t-PA, which has a threonine (T) replaced by an asparagine at amino acid position 103, adding a glycosylation site at that position, an asparagine (N) replaced by glutamine at position 117, removing a glycosylation site at that position, and four amino acids, lysine (K); histidine (H), arginine (R), and arginine (R) replaced by four alanines (A,A,A,A) at amino acid positions 296–299. A large scale clinical trial (ASSENT-II) has shown TNKase™ (tenecteplase) to be the optimal thrombolytic agent, due to its ease of single-bolus administration, equivalent mortality to t-PA, and lower bleeding risk, as a result of its improved fibrin specificity (ASSENT-II Investigators, *Lancet* 354:716–22 (1999)). While of all thrombolytic agents tested, TNKase™ (tenecteplase) has been found to have the highest fibrin specificity, and its extended half-life allows single bolus dose administration, there is room for further improvement by way of improving efficacy without increasing the risk of side-effects, such as intracranial bleeding and stroke. For safety of a single bolus administration of tenecteplase see also Van de Werf et al., *Am. Heart J.* 137:786–91 (1999).

SUMMARY OF THE INVENTION

The present invention concerns an improved therapeutic regimen for fibrinolytic therapy. In particular, the invention concerns the combined administration of a t-PA variant suitable for single-dose administration and an antithrombin agent having anti-Xa and/or anti-IIa activity, such as a low molecular weight heparin.

Accordingly, in one aspect, the invention concerns a method comprising administering to a human patient in need of thrombolytic therapy an effective amount of a combination of a human tissue plasminogen activator (ht-PA) variant suitable for single-bolus administration, and a low molecular weight heparin.

In one embodiment, the ht-PA variant is glycosylated at any of positions 103–105, and devoid of functional carbohydrate structure at position 117 of wild-type ht-PA amino acid sequence, and exhibits a) extended circulatory half-life and substantially retained fibrin-binding, or improved in vivo fibrinolytic potency, and b) improved fibrin specificity, as compared to wild-type ht-PA. Preferably, the ht-PA variant has extended circulatory half-life and substantially retained fibrin binding as compared to wild-type ht-PA. In another preferred embodiment, the ht-PA variant has improved in vivo fibrinolytic potency as compared to wild-type ht-PA.

One of the representative t-PA variants useful in the treatment method of the present invention has an N-linked glycosylation at position 103 of the wild-type ht-PA amino acid sequence. In a preferred t-PA variant, there is asparagine as part of an Asn-X-Ser or Asn-X-Thr tripeptidyl sequence, wherein Asn is asparagine, Ser is serine, Thr is threonine, and X is any amino acid except proline, at position 103 of the wild-type ht-PA amino acid sequence. Another t-PA variant has asparagine at position 103, tryptophane at position 104, and serine at position 105 of the wild-type ht-PA amino acid sequence.

ht-PA variants which additionally have an amino acid other than asparagine at position 117 of the wild-type ht-PA amino acid sequence can be advantageously used in the treatment methods herein. It is further of advantage to make further alterations within the wild-type ht-PA amino acid sequence in order to improve fibrin-specificity, relative to wild-type ht-PA. Such alterations preferably are in the serine protease domain of wild-type ht-PA, in particular within the amino acid region 296–302 or 274–277 of the wild-type ht-PA amino sequence. ht-PA variants having an alteration (preferably amino acid substitution) in the region 296–299 of the wild-type h-t-PA amino acid sequence are particularly preferred. In a specific variant, the alteration is the substitution of alanine for each of amino acids lysine, histidine, arginine, and arginine at respective positions 296, 297, 298, and 299 of the wild-type ht-PA amino acid sequence.

The treatment method of the present invention can be carried out with a variety of low molecular weight heparin preparations, including, for example, enoxaparin, dalteparin, tinzaparin, certoparin, pamaparin, nadroparin, ardeparin, and reviparin. A preferred low molecular weight heparin is enoxaparin.

Administration of the low molecular weight heparin and ht-PA variant should take place as soon as possible following the onset of symptoms indicating that thrombolytic therapy is required. Thus, administration should preferably take place within about 8 hours, more preferably within about 6 hours, even more preferably within about 4 hours following the onset of symptoms.

The ht-PA variant and the low molecular weight heparin can be administered simultaneously or in either order, following conventional routes of administration. In a specific embodiment, the low molecular weight heparin is administered first, followed by administration of the ht-PA variant as a weight-adjusted single bolus.

The low molecular weight heparin, e.g. enoxaparin, is typically administered as an intravenous bolus followed by subcutaneous administration, where the subcutaneous administration may be repeated in periodic intervals in order to reduce the likelihood of reocclusion. Thus, enoxaparin may be administered as an intravenous bolus of about 30 mg immediately followed by a subcutaneous dose of about 1 mg/kg.

The condition to be treated can be any condition requiring thrombolytic therapy, such as, for example, myocardial infarction (MI), venous thrombosis, pulmonary embolism, cerebrovascular accident, and arterial embolism.

DETAILED DESCRIPTION OF THE PREFERRED EMBODIMENT

A. Definitions

The terms "wild-type human tissue plasminogen activator," "wild-type human t-PA," and "wild-type ht-PA" as used herein, refer to human extrinsic (tissue-type) plasminogen activator having fibrinolytic activity that typically has a structure with five domains (finger, growth factor, Kringle-1, Kringle-2, and protease domains). The nucleotide and amino acid sequences of wild-type (native) human t-PA have been reported by Pennica et al., Nature 301:214 (1983) and in U.S. Pat. No. 4,766,075, issued Aug. 23, 1988. The location of a particular amino acid in the polypeptide chain of t-PA is identified by a number. The number refers to the amino acid position in the amino acid sequence of the mature, wild-type human t-PA polypeptide as disclosed in U.S. Pat. No. 4,766,075. In the present application, similarly positioned residues in t-PA variants are designated by these numbers even though the actual residue number is not so numbered due to deletions or insertions in the molecule. This will occur, for example, with deletional or insertional variants. The amino acids are identified using the one-letter or three-letter code. Substituted amino acids are sometimes designated herein by identifying the wild-type amino acid on the left side of the number denoting the position in the polypeptide chain of that amino acid, and identifying the substituted amino acid on the right side of the number. For example, replacement of the amino acid threonine (T) by asparagine (N) at amino acid position 103 of the wild-type human t-PA molecule yields a t-PA variant designated T103N t-PA. Similarly, the t-PA variant obtained by additional substitution of glutamine (Q) for asparagine (N) at amino acid position 117 of the wild-type human t-PA molecule is designated T103N, N117Q t-PA. Deletional variants are identified by indicating the amino acid residue and position at either end of the deletion, inclusive, and placing the Greek letter delta, "Δ", to the left of the indicated amino acids. Insertional t-PA variants are designated by the use of brackets "[ ]" around the inserted amino acids, and the location of the insertion is denoted by indicating the position of the amino acid on either side of the insertion.

The various domains within the wild-type human t-PA (ht-PA) amino acid sequence have been designated, starting at the N-terminus of the amino acid sequence of human tissue plasminogen activator, as 1) the finger region (F) that has variously been defined as including amino acid 1 upwards of about 44, 2) the growth factor region (G) that has been variously defined as stretching from about amino acid 45 upwards of amino acid 91 (based upon its homology with EGF), 3) Kringle-1 (K1) that has been defined as stretching from about amino acid 92 to about 173, 4) Kringle-2 (K2) that has been defined as stretching from about amino acid 180 to about amino acid 261 and 5) the so-called (serine) protease domain (P) that generally has been defined as stretching from about amino acid 264 to the C-terminal end of the molecule. These domains are situated contiguously generally of one another, or are separated by short "linker" regions, and account for the entire amino acid sequence from about 1 to 527 amino acids in its putative mature form.

The term "human tissue plasminogen activator variant" or "ht-PA variant" is used to refer to a tissue plasminogen activator, which differs from wild-type ht-PA at at least one amino acid position, and retains a functional fibrin binding region and serine protease domain. The finger (F), growth factor (GF), and (to a lesser extent) Kringle-2 (K2) domains of wild-type ht-PA are known to be involved in fibrin binding. An ht-PA variant having a functional fibrin binding region will retain at least the minimal sequences of these domains that are required for fibrin binding. The serum protease domain is responsible for the enzymatic activity for wild-type ht-PA. An ht-PA variant having a functional serine protease domain retains at least the minimal sequences from the serine protease domain of wild-type ht-PA required for converting plasminogen to plasmin in the presence of a plasma clot or in the presence of fibrin.

The terms "TNK t-PA," "T103N, N117Q, KHRR (296–299)AAAA t-PA," "tenecteplase," and "TNKase™," are used interchangeably and designate a human t-PA variant, which has a threonine (T) replaced by an asparagine at amino acid position 103, adding a glycosylation site at that position, an asparagine (N) replaced by glutamine at position 117, removing a glycosylation site at that position, and four amino acids, lysine (K), histidine (H), arginine (R), and arginine (R) replaced by four alanines (A,A,A,A) at amino acid positions 296–299 of the wild-type human t-PA amino acid sequence. TNKase™ (Genentech, Inc., South San Francisco, Calif.) has been approved by the FDA for use in the reduction of mortality associated with AMI as a single intravenous bolus.

The terms "low molecular weight heparin" and "LMW heparin" are used interchangeably, and refer to heparin fractions typically prepared by fractionation and/or depolymerization of heparin so as to achieve significant reduction in average molecular weight as compared with whole heparin preparations. Compositions containing, procedures for making, and methods for using low molecular weight heparin are described in various patent publications, including U.S. Pat. Nos. 4,281,108, 4,687,765, 5,106,734, 4,977,250, 5,576,304, and EP 372 969, the contents of which are hereby expressly incorporated by reference. LMW heparins for use in the present invention preferably have an average molecular weight of about 10 kD or less, more preferably of about 8 kD or less, most preferably less than about 5 kD. It is further preferred that LMW heparins should be of relatively uniform molecular weight e.g. with at least about 60%, more preferably at least about 80% of polymer units having a molecular weight within the above defined average molecular weight limits.

The terms "fibrin binding" and "fibrin binding affinity" refer to the ability of the t-PA molecule to bind fibrin clots in standard fibrin binding assays, such as the method described by Rijken et al., J. Biol. Chem. 257, 2920–2925 (1982) or its modified versions known in the art.

The terms "(t-PA) biological activity", "biologically active", "activity" and "active" refer to the ability of the t-PA molecule to convert plasminogen to plasmin in the presence of a plasma clot or in the presence of fibrin, as measured by the S-2288 assay, the plasma clot lysis assay, or other appropriate assays. The assay(s) may be conducted in the presence or absence of potential modulators of activity such as fibrin, fibrinogen, plasma and/or plasma clots.

The expressions "fibrinolytic activity", "thrombolytic activity" and "clot lysis activity" are used interchangeably and refer to the ability of a t-PA molecule to lyse a clot, whether derived from purified fibrin or from plasma, using any in vitro clot lysis assay known in the art, such as the purified clot lysis assay by Carlson, R. H. et al., Anal. Biochem. 168, 428–435 (1988) and its modified form described by Bennett, W. F. et al., J. Biol. Chem. 266 5191–5201 (1991).

The expressions "in vivo fibrinolytic potency", "in vivo thrombolytic potency" and "in vivo clot lysis potency" are used interchangeably and refer to clot lysis per unit dose of t-PA. "In vivo fibrinolytic potency" is determined in any accepted animal model of clot lysis assay, including the hamster pulmonary embolism model (Collen, D. et al., Thromb. Haemost. 65:174–180 (1991)), and the rabbit jugular vein thrombosis model (Collen, D. et al., J. Clin. Invest. 71:368–376 (1983)).

The expression "substantially retain fibrin binding (affinity)", (compared to wild-type human t-PA) and grammatical variants thereof as used herein mean that the fibrin binding affinity (apparent $K_d$ value) of the variant t-PA molecule is within about two fold of the fibrin binding affinity ($K_d$ value) for wild-type human t-PA as determined in the same assay. The expression "substantially improved fibrin binding" refers to a greater than about four fold increase in the fibrin binding affinity (apparent $K_d$ value) of a t-PA variant, as compared to that of wild-type t-PA, caused by the inclusion of an additional mutation or set of mutations. The term "improved in vivo fibrinolytic potency" compared to wild-type t-PA refers to comparable in vivo clot lysis achieved by the administration of a variant t-PA at about one-third or less the dose of wild-type t-PA.

The terms "clearance rate" and "clearance" refer to the rate at which the t-PA molecule is removed from the bloodstream. Clearance (rate) is measured with respect to native t-PA, such that decreased clearance (rate) indicates that the t-PA variant is cleared more slowly than native t-PA, and increased clearance (rate) indicates that the t-PA variant is cleared more rapidly than native t-PA.

The term "circulatory half-life" means the half-life of a polypeptide of interest or polypeptide variant (e.g. an ht-PA variant) circulating in the blood of a given mammal.

The expression "higher fibrin specificity" refers to the activity of a t-PA variant that exhibits a higher ratio of fibrin-dependent specific activity to fibrinogen-dependent specific activity in a S-2251 assay (in either the one-chain or two-chain form) than wild-type rt-PA, and preferably a ratio of at least about 1.5.

The expression "higher plasma clot specificity" refers to the activity of a t-PA variant that exhibits a higher ratio of plasma clot-dependent specific activity to plasma-dependent specific activity in a S-2251 assay (in either the one-chain or two-chain form) than wild-type rt-PA, and preferably a ratio of at least about 1.5.

The expression "devoid of functional carbohydrate structure at amino acid position 117 of wild-type human t-PA" means complete removal of the carbohydrate at amino acid residue 117, as where the glycosylation signal is destroyed by site-directed mutagenesis, or substantial removal, as by treatment with an endoglycosidase which may leave an intact N-acetylglucosamine residue linked to Asn 117, for example.

The term "thrombolytic disorder" is used in the broadest sense and refers to any condition characterized by the formation of a thrombus that obstructs vascular blood flow locally or detaches and embolizes to occlude blood flow downstream (thromboembolism). Thrombolytic disorders specifically include, without limitation, myocardial infarction (MI), venous thrombosis, pulmonary embolism, cerebrovascular accident, arterial embolism, etc.

The term "myocardial infarction" or "MI" is used to refer to ischemic myocardial necrosis usually resulting from abrupt reduction in coronary blood flow to a segment of myocardium. MI is typically a disease of the left ventricle (LV), but damage may extend to the right ventricle (RV) or atria.

The term "venous thrombosis" is used to include all forms of thrombosis, such as thrombosis affecting the superficial veins (superficial thrombophlebitis) and deep vein thrombosis (DVT). Since thrombosis is virtually always accompanied by phlebitis, the terms "thrombosis" and "thrombophlebitis" are used interchangeably.

"Pulmonary embolism" is the sudden lodgment of a blood clot in a pulmonary artery with subsequent obstructed blood supply to the lung parenchyma. The most common type of pulmonary embolus is a thrombus that usually has migrated from a leg or pelvic vein. Most of those that cause serious hemodynamic disturbances form in an iliofemoral vein, either de novo or by propagation from calf vein thrombi. Thromboemboli originate infrequently in the arm veins or in the right cardiac chambers.

The term "cerebrovascular accident" is used to refer to stroke and, in general, infarction due to embolism or thrombosis of intracranial or extracarnial arteries, and associated hemorrhage.

"Coronary patency" is evaluated by angiography, using Thrombolysis In Myocardial Infarction (TIMI) criteria. The TIMI flow grades are defined as follows: TIMI flow 0=no perfusion; TIMI flow 1=penetration without perfusion; TIMI flow 2=partial perfusion with delayed run-off; TIMI flow 3=complete perfusion with brisk run-off.

The term "antithrombotic therapy" refers to therapy aimed at preventing the formation or growth of a blood clot, or partial or complete dissolution of a blood clot already formed.

The terms "treat" or "treatment" refer to both therapeutic treatment and prophylactic or preventative measures, wherein the object is to prevent, slow down (lessen), or reverse an undesired physiological change or disorder, such as the formation of a blood clot and the development of other physiological changes associated with the formation of blood clots, e.g. restenosis; reocclusion; hemorrhage; hemodynamic disturbances; pain, arrhytmias, sinus node disturbances, atrioventricular block, etc. associated with MI. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, the phrase "effective amount" or "therapeutically effective amount" is intended to include an amount of a compound or combination of compounds, as applicable, to treat a thrombolytic disorder in a mammal, including humans. The combination of compounds may be, but does not have to be, a synergistic combination. "Synergy" as described, for example, by Chou and Talalay, *Adv. Enzyme Regul.* 22:27–55 (1984), occurs when the effect (in the present case the thrombolytic effect) of the compounds when administered in combination is greater than the additive effect of the compounds when each is administered alone, as a single agent.

The term "mammal" refers to any animal classified as a mammal, including humans, domestic and farm animals, and zoo, sports, or pet animals, such as mouse, rat, rabbit, pig, sheep, goat, cattle and higher primates.

The terms "combination," "combined" and similar expressions, when used in reference to the administration of two or more compounds, mean that the compounds are administered to a subject concurrently. Concurrent administration includes administration at the same time, in the same formulation or separately, and sequential administration in any order or at different points in time so as to provide the desired therapeutic effect.

B. Detailed Description

According to the World Health Organization, cardiovascular diseases account for 12 million deaths in the world each year. Currently, heart attack is a leading killer of men and women in developed countries. It is projected that by 2010, heart disease will be the number one cause of death in developing countries.

In the last decade, thrombolytic therapy has emerged as the standard of care for the pharmacological management of thrombolytic diseases, such as AMI. However, despite recent advances, most current thrombolytic regimens have significant shortcomings due to (1) low optimal reperfusion rate (TIMI grade 3 flow in about 50% of patients treated), (2) time delay to reperfusion averaging 45–120 minutes, (3) reocclusion of the infarct-related artery after initial successful reperfusion in 5–10% of the patents treated and associated increased mortality; and intracranial bleeding in up to 0.9% of patients treated. See, e.g. Jang et al., *J. Am. Coll. Cardiol.* 33:1879–85 (1999). In order to further improve treatment outcomes, cardiologists throughout the world are investigating various combinations of thrombolytic agents combined with other pharmacological agents, such as antithrombotics and anti-platelet agents, in an attempt to maximize artery-opening patency and reduce mortality.

The present invention concerns an improved therapy regimen for the treatment of thrombolytic disorders, such as acute myocardial infarction (AMI). In particular, the invention is concerned with a new and improved combination therapy using a long half-life, fibrin specific t-PA variant (e.g. TNK t-PA) in combination with a low molecular weight heparin. The new treatment regimen combines improved efficacy and safety when compared with other therapeutic approaches currently used in clinical practice.

B.1 Tissue Plasminogen Activator (t-PA) Variants

As discussed above, TNK t-PA (TNKase™, tenecteplase; T103N, N117Q, KHRR(296–299)AAAA t-PA) is a 527 amino acids long glycoprotein developed by Genentech, Inc., which obtained FDA approval on Jun. 2, 2000 for use in the reduction of mortality associated with acute myocardial infarction (AMI). TNKase™ (tenecteplase) is a derivative of wild-type human t-PA, which has a threonine (T) replaced by an asparagine at amino acid position 103, adding a glycosylation site at that position, an asparagine (N) replaced by glutamine at position 117, removing a glycosylation site at that position, and four amino acids, lysine (K), histidine (H), arginine (R), and arginine (R) replaced by four alanines (A,A,A,A) at amino acid positions 296–299. In the 113 patient TIMI 10A trial, TNK t-PA was shown to have a prolonged half-life that allows it to be administered as a single intravenous (IV) bolus (Cannon et al., *Circulation* 95:351–6 (1997)). Due to this property, TNK t-PA is particularly suitable for pre-hospital administration.

In the TIMI 10B trial, an angiographic study with 886 patients, TNK t-PA was demonstrated to have similar patency and TIMI flow as wild-type human t-PA. Wild-type t-PA was administered as a 15 mg bolus of t-PA, a 0.75 mg/kg (up to 50 mg) infusion over 30 minutes, followed by 0.50 mg/kg (up to 35 mg) infusion over 60 minutes. The 60-minute and 90-minute TIMI flow data are shown in the following Tables 1 and 2.

TABLE 1

| Drug/dose | 60 min TIMI flow grade 2 and 3 | 6-min TIMI flow grade 3 | 60 min median corrected TIMI frame count (n) |
|---|---|---|---|
| TNK t-PA 30 mg (N = 176) | 78% | 48% | 37 |
| TNK t-PA 40 mg (n = 84) | 79% | 58% | 37 |
| TNK-t-PA 50 mg (n = 42) | 79% | 45% | 37 |
| t-PA (n = 65) | 78% | 48% | 40 |

TABLE 2

| Drug/dose | 90 min TIMI flow grade 2 and 3 | 90 min TIMI flow grade 3 | 90 min corrected median TIMI frame count |
|---|---|---|---|
| TNK t-PA 30 mg (n = 297) | 76% | 55% | 38 |
| TNK t-PA 40 mg (n = 131) | 79% | 64% | 30 |
| TNK t-PA 50 mg (n = 42) | 88% | 66% | 34 |
| t-PA (n = 303) | 82% | 63% | 33 |

In addition, of all thrombolytic agents tested in large clinical trials, TNK t-PA has the highest fibrin specificity. In the TIMI 10A trial, systemic fibrinogen and plasminogen levels in patients treated with TNK t-PA fell by only 5–10% at 1 and 3 hours following administration (Tanswell et al., *J. Am. Coll. Cardiol.* 19:1071–5 (1992)).

Based on its uniquely advantageous properties, such as easy administration as a single rapid bolus, equivalence compared to wild-type t-PA with respect to mortality and intracranial hemorrhage, and lower rates of major bleeding side-effects, TNK t-PA is a new standard for thrombolytic therapy.

Although the invention will be illustrated by data obtained with TNK t-PA, it is contemplated that other ht-PA variants with similar properties can be used in the treatment methods herein. In general, the use of any ht-PA variant suitable for single bolus administration is specifically within the scope of the present invention. The relatively rapid clearance of wild-type ht-PA from the plasma, while it is an advantage in patients needing emergency intervention after an event involving thrombus formation, e.g. MI, requires continuous intravenous administration to maintain therapeutic levels of t-PA in the blood stream. Variants of wild-type ht-PA that are suitable for single bolus administration are required to have extended circulatory half-life (decreased clearance) compared to wild-type ht-PA. In addition, it is desirable that such variants have improved fibrin-specificity relative to wild-type ht-PA in order to reduce the likelihood of bleeding incidence associated with bolus administration. ht-PA variants meeting these requirements are disclosed, for example, in EP 643,772, the entire disclosure of which is hereby expressly incorporated by reference.

An exemplary ht-PA variant developed for single-bolus administration is lanoteplase (nPA), a deletion variant lacking the finger and epidermal growth factor domains of wild-type ht-PA (*The TIME-II Investigators, Eur. Heart J.* 21:2005–2013 (2000)). This ht-PA variant, developed by Genetics Institute and licensed to Bristol-Myers Squibb and Suntory, has a longer circulatory half-life than wild-type ht-PA but is less fibrin specific. See also Umemura et al., *Eur. J. Pharmacol.* 262:27–31 (1994). The use of lanoteplase is specifically within the scope herein. Other t-PA variants developed for bolus administration and having longer circulatory half-lives than wild-type ht-PA include monteplase (Kawai et al., *J. Am. Col. Cardiol.* 29:1447–1453 (1997)), in which Cys84 of wild-type ht-PA is substituted by Ser, pamiteplase (Kawasaki et al., *Drug. Dev. Res.* 33:33–38 (1994)), having amino acids 92 to 173 of wild-type ht-PA deleted, an Arg275 substituted by Glu, and a truncated t-PA variant D-K2P (Saito et al., *Biotechnol. Prog.* 10:472–479 (1994)), missing the finger and EGF domains.

Further exemplary ht-PA variants suitable for use in the combination therapy of the present invention are glycosylated at any of positions 103–105 and lack functional carbohydrate structure at amino acid position 117 of wild-type ht-PA. The removal of the functional carbohydrate structure can be accomplished by any method known in the art, but preferably is achieved by amino acid substitution for at least one residue in the Asn-Ser-Ser glycosylation signal at positions 117–119 of the wild-type ht-PA amino acid sequence. In a particularly relevant variant, asparagine at amino acid position 117 is replaced by another amino acid, the preferred substituent being glutamine (see, also EP 238,304; WO 89/04368; and U.S. Pat. No. 5,612,029). In addition, the carbohydrate structure at amino acid position 117 of wild-type ht-PA can be substantially removed by the use of an endoglycosidase, such as Endoglycolidase H (Endo-H). Endo-H is only capable of removal of high mannose and hybrid oligosaccharides. Accordingly, under appropriate conditions, Endo-H is capable of substantially removing the high mahnose carbohydrate structure at amino acid residue 117 of wild-type ht-PA, without functionally affecting the complex structures at amino acid residues 184 and 448.

Glycosylation in the 103–105 amino acid region is preferably accomplished by creating an N-linked glycosylation signal at any of these positions. In particular, such variants will have asparagines as part of an Asn-X-Ser, or Asn-X-Thr tripeptidyl sequence (X is any amino acid other than proline) at position 103, 104, or 105 of the wild-type ht-PA amino acid sequence. The added N-linked glycosylation preferably is at position 103. Such ht-PA variants will have an asparagine at position 103, tryptophan at position 104, and serine at position 105 of the wild-type ht-PA amino acid sequence.

As discussed above, it is particularly desirable to use in the combination therapy herein t-PA variants that are more fibrin-specific than wild-type ht-PA. Such ht-PA variants will act more preferentially at the site of the fibrin clot than wild-type ht-PA and are, therefore, expected to cause diminished side-effects associated with the activation of circulating plasminogen, e.g. less severe and less frequent bleeding complications. Improved fibrin specificity can be achieved by an alteration known in the art. Fibrin specificity can be improved, for example, by amino acid alterations within the serine protease domain of wild-type ht-PA. The amino acid alterations may be, for example, substitutions at one or more of amino acid positions 296–302, preferably 296–299 of the serine protease domain. In a preferred variant, each of the amino acids lysine, histidine, arginine, arginine at positions 296–299 of wild-type ht-PA is replaced by alanine. In a further preferred variant, the arginines at positions 298 and 299 are both replaced by glutamic acid. In another preferred variant, the lysine, histidine, and proline at amino acid positions 296, 297 and 302 of wild-type ht-PA are additionally replaced by glutamine, asparagine, and serine, respectively. In a further fibrin-specific variant, phenylalanine, arginine, isoleucine, and lysine at amino acid positions 274, 275, 276 and 277 of the wild-type ht-PA amino acid sequence are replaced by amino acids leucine, histidine, serine, and threonine, respectively. The latter alteration results in a loss of plasmin cleavage site, therefore, the variants are substantially in a single chain form.

In addition to the alterations resulting in enhanced circulatory half-life and/or increased fibrin-specificity relative to wild-type ht-PA, the t-PA variants may contain additional amino acid alterations, e.g. substitutions, insertions and/or deletions to further improve their therapeutic properties.

Examples of suitable t-PA variants for use in accordance with the present invention include T103N, N117Y t-PA; S105N, A107S, N117Z t-PA; S105N, A107S, N117Z t-PA; T103N, N117Z, KHRR(296–299)AAAA t-PA; S105N, A107S, N117Z KHRR(296–299)AAAA t-PA; T103N, N117Z, R298E, R299E t-PA; S105N, A107S, N117Z, R298E, R299E t-PA; T103N, N117Z, K296Q, H297N, P301S t-PA; S105N, N117Z, K296Q, H297N, P301S t-PA; T103N, N117Z, FRIK(274–277)LHST t-PA; S105N, A107S, N117Z, FRIK(274–277)LHST t-PA, wherein Z denotes any of the 20 naturally occurring amino acids, except asparagine (N). Particularly preferred are the ht-PA variants in which at position 117 asparagine (N) is substituted by glutamine (Q).

Tenecteplase is commercially available from Genentech, Inc., South San Francisco, Calif. The other ht-PA variants can be readily prepared by well known techniques of recombinant DNA technology and/or chemical synthesis.

The plasma clearance and fibrin specificity of the t-PA variants can be tested, for example, as described by Paoni et al., *Thrombosis and Haemostasis* 70:307–312 (1993); Keyt et al., *Proc. Natl. Acad Sci. USA* 91:3670–3674 (1994); Refino et al., *Thrombosis and Haemostasis* 70:313–319 (1993); or using a rabbit thrombosed carotid artery model described by Benedict et al., *Circulation* 92:3032–3040 (1995). Plasma clearance, fibrin binding, and clot lysis activity can also be tested as described in EP 643,772. The results obtained can then be confirmed in human clinical trials, similar to those conducted for tenecteplase, such as, for example, the ASSENT-II study reported in, *Lancet* 354:716–22 (1999).

B.2 Low Molecular Weight Heparin

Antithrombin therapy for patients receiving thrombolytics is believed to be important to both inhibit thrombin that is already present prior to thrombolysis and that which is generated as a consequence of administration of a thrombolytic. Thrombin is one of the main stimuli responsible for platelet activation in the setting of thrombolysis and plays a central role in the pathogenesis or coronary rethrombosis. Although standard antithrombin therapy with intravenous unfractionated heparin is able to inhibit thrombin activity, it is less effective in the inhibition of thrombin regeneration. Around 50 to 60% of patients has either suboptimal or inadequate anticoagulation with unfractionated heparin during thrombolysis, and when more intensive unfractionated heparin regimens were tested, an increased rate of hemorrhages, including intracerebral hemorrhages, were observed (Antman, E. M., *Circulation* 90:1624–30 (1994); *The Global Use of Strategies to Open Occluded Coronary Arteries (GUSTO) II a Investigators, Circulation* 90:1631–7 (1994)).

Low molecular weight heparins (LMWHs) are obtained from standard unfractionated heparin (UFH), and have been used for the prophylaxis and treatment of venous thromboembolism (see, e.g. Schafer, A. I., *Hospital Practice* Jan. 15, 1997, pp. 99–106). LMWHs have also be used in the treatment of unstable angina and non-Q wave myocardial infarction. Commercially available low molecular weight heparins include, for example LOVENOX® (enoxaparin sodium injection, available from Aventis Pharma Inc. (Bridgewater, N.J.), described in U.S. Pat. No. 5,389,618), FRAGMIN™ (dalteparin sodium injection, available from Pharmacia, Inc. (Columbus, Ohio)), INNOHEP® (tinzaparin sodium, available from DuPont Pharmaceuticals Company (Wilmington, Del.)), ALPHAPARIN™ (certoparin, available from Alpha, U.K.), FRAXIPARINE™ (nadroparin calcium, available from Sanofi-Synthelabo Canada, Inc.), NORMIFLO™ (ardeparin, available from Wyeth Laboratories, U.S.), and CLIVARINE™ (reviparin sodium, available from ICN Pharmaceuticals).

A particularly advantageous low molecular weight heparin preparation is LOVENOX® (enoxaparin sodium injection), hereinafter referred to as "enoxaparin." Enoxaparin is a low molecular weight heparin produced by depolymerization of standard unfractionated heparin (UFH). Unlike porcine UFH, which has a molecular weight of 12,000 to 15,000 Daltons, enoxaparin has an average molecular weight of 4,500 Daltons. Compared to UFH, it has more predictable pharmacokinetics, and a higher ratio of anti-Factor Xa to anti-Factor IIa activity. Enoxaparin is also resistant to inactivation by platelet factor 4. In studies examining enoxaparin in acute coronary syndrome patients, enoxaparin has been shown to be safe and more effective than unfractionated heparin at reducing coronary events (Cohen et al., *N. Engl. J. Med.* 337:447–52 (1997); Antman. E. M. and Women's Hosp., Boston, Mass., *Supplement to Circulation* 17:504–2649 (1998)).

B.3 Combination Therapy

The ht-PA variants and low molecular weight heparin used herein can be formulated according to known methods to prepare pharmaceutical compositions, whereby the active ingredient is combined with a pharmaceutically acceptable carrier. The ht-PA variant formulations include sterile aqueous solutions and sterile hydratable powders, such as lyophilized formulations. Typically, an appropriate amount of a pharmaceutically acceptable salt is also used in the formulation to render the formulation isotonic. A buffer, such as arginine base, in combination with phosphoric acid is also typically included at an appropriate concentration to maintain a suitable pH, generally from about 5.5 to about 7.5. In addition or alternatively, a compound such as glycerol may be included in the formulation to help maintain the shelf-life.

Tenecteplase is currently marketed as a sterile, white to off-white, lyophilized powder for single IV administration after reconstitution with Sterile Water for Injection (SWFI). Each vial of the commercial formulation of tenecteplase (TNKase™) nominally contains 52.5 mg tenecteplase, 0.55 g L-arginine, 0.17 g phosphoric acid, and 4.3 mg polysorbate 20, which includes a 5% overfill, and each vial delivers 50 mg of tenecteplase. The reconstituted solution contains 5 mg/mil tenecteplase. However, other pharmaceutical formulations are also specifically within the scope of the present invention.

The t-PA variants of the present invention are typically administered as a single (occasionally repeated) intravenous (IV) bolus, in combination with a low molecular weight heparin, which is typically administered intravenously and/or subcutaneously (SC). Bolus administration has several advantages. The ease of administration facilitates early intervention and may make more feasible prehospital treatment with thrombolysis, and the simplicity of dosing may reduce medication errors, thereby reducing associated mortality.

In the treatment of thrombolytic disorders, such as MI, the t-PA variant, such as TNK t-PA (TNKase™, tenecteplase), hereinafter referred to as "tenecteplase," is preferably administered as a single intravenous (IV) bolus, in combination with a low molecule weight heparin, such as LOVENOX® (enoxaparin sodium injection), hereinafter referred to as "enoxaparin." A typical dose for a t-PA variant such as tenecteplase is between about 15 mg and about 50 mg, depending on the body weight of the patient, although lower and higher doses are also envisioned. The optimal dose depends on factors like the thrombolytic disorder targeted, the patient's sex, age, overall physical condition, the severity of the disease, and the like. The determination of the optimal dose is well within the skill of an ordinary physician. In a typical situation, to a patient weighing between about 70 and 80 kg, a t-PA variant such as tenecteplase is typically administered in a dose of about 40 mg, as a single IV bolus over 5–10 seconds, preferably over 5 seconds. For more precise, weight-adjusted dosing of the t-PA variant, see also Gibson et al., *Am. J. Cardiol.* 84:976–980 (1999). Weight adjusted dose typically varies between about 0.2 mg/kg of body weight and about 1.25 mg/kg of body weight.

Low molecular weight heparin, such as enoxaparin, is typically administered in conjunction with the t-PA variant, such as tenecteplase, starting with a fixed IV bolus followed by weight adjusted subcutaneous (SC) injections. For example, the low molecular weight heparin such as enoxaparin can be administered as a single IV bolus, followed by SC injections. In a typical dosing regimen, a single IV bolus of about 30 mg low molecular weight heparin (e.g. enoxaparin) is followed by about 1 mg/kg SC injections about every 12 hours. In a typical situation, the first SC injection immediately follows the IV bolus, and treatment follows until the patient's discharge, or until revascularization, or for 7 days, whichever comes first. Just as with the t-PA variant, e.g., tenecteplase, the IV and SC doses of the low molecular weight heparin (e.g. enoxaparin) are determined to match the targeted thrombolytic disorder, the patient's age, sex, overall physical condition, weight, and the like.

More specifically, patients are typically given enoxaparin at about 30 mg if their body weight is less than about 60 kg, about 35 mg if it is about 60–69 kg, about 40 mg if it is about 70–79 kg, about 45 mg if it is about 80–89 kg, and about 50 mg if it is about 90 kg or more.

In a large-scale clinical study (ASSENT-3), enrolling 6,095 heart attack patients at more than 500 sites worldwide, details of which are provided in the Examples below, combination treatment with tenecteplase and enoxaparin resulted not only in improved clinical efficacy and safety benefits, but also yielded an exceptionally low 30-day mortality rate (5.35%). This is the lowest reported mortality rate reported to date in a large-scale clinical trial of acute myocardial infarction.

Thrombolytic therapy with a combination of an ht-PA variant and a low molecular weight heparin in accordance with the present invention may be combined with the administration of aspirin as early as possible following the thrombotic event, and other therapeutic agents, such as β-blockers, calcium channel blockers, angiotensin-converting enzyme (ACE) inhibitors, intravenous nitrates, β-blockers, angiotensin II inhibitors, statins, ticlopidin/clopidogrel, oral anticoagulants, Abciximab, other gpIIb/IIIa inhibitors, angiotensin-receptor blockers, thienopyridines, and thrombolytics, all conventionally used in cardiac treatment.

Further details of the invention are provided in the following non-limiting example.

All literature and other citations throughout this application are hereby expressly incorporated by reference.

EXAMPLE

Efficacy and Safety of Tenecteplase in Combination with Enoxaparin in the Treatment of Myocardial Infarction Patients and Methods Patients in 575 hospitals in 26 countries were recruited. Inclusion criteria were identical to those of the Assessment of the Safety and Efficacy of a New Thrombolytic Regimen (ASSENT)-2 trial (*Lancet* 354:716–22 (1999)), i.e. age 18 years or older, onset of symptoms less than 6 h before randomization, ST-segment elevation of at least 0.1 mV in two or more limb leads or at least 0.2 mV in two or more contiguous pericardial leads, or left bundle-branch block. Exclusion criteria on admission were: systolic blood pressure of more than 180 mm Hg, diastolic blood pressure of more than 110 mm Hg, or both on repeated measurements; use of abciximab or other glycoprotein IIb/IIIa inhibitors within the preceding 7 days; major surgery, biopsy of a parenchymal organ or substantial trauma within 2 months; any head injury or other trauma occurring after onset of current myocardial infarction; any known history of stroke, transient ischemic attack, or dementia; any known structural damage to the central nervous system; current treatment with oral anticoagulants; treatment with unfractionated heparin of more than 5000 U or a therapeutic subcutaneous dose of low-molecular-weight heparin within 6 h; known thrombocytopenia (<100 000 cells/μL); known renal insufficiency (serum creatinine concentration >221 μmol/L for men and >177 μmol/L for women); sustained cardiopulmonary resuscitation (more than 10 min) in previous 2 weeks; pregnancy, lactation, or parturition in the previous 30 days; active participation in another investigative drug or device study in the previous 30 days; previous enrollment in this study; any other disorder that would place the patient at increased risk; and inability to follow the protocol and to comply with the follow-up requirements.

The protocol was approved by each hospital's institutional review board, and patients gave informed consent.

Patients were randomly assigned, via a central computerized telephone system into one of the following three groups:

Group I: a bodyweight-adjusted single bolus of tenecteplase with enoxaparin (enoxaparin group), Group II: low-dose tenecteplase, plus abciximab, plus low-dose unfractionated heparin (abciximab group), Group III: full-dose tenecteplase with weight-adjusted unfractionated heparin (heparin group).

Each patient was given a unique study number that corresponded with the number of a treatment kit. Study treatments were given on an open-label basis.

Tenecteplase was given over 5 seconds according to bodyweight: patients assigned enoxaparin or unfractionated heparin were given 30 mg if their bodyweight was less than 60 kg, 35 mg if it was 60–69 kg, 40 mg if it was 70–79 kg, 45 mg if it was 80–89 kg, and 50 mg if it was 90 kg or more. In patients assigned combination treatment with abciximab, half-dose tenecteplase was given with doses ranging from 15 mg to 25 mg according to the same weight categories as with the full dose.

Patients assigned weight-adjusted intravenous unfractionated heparin received a bolus of 60 U/kg (maximum of 4000 U) and initial infusion of 12 U/kg per h (maximum 1000

U/h) adjusted to maintain an activated partial thromboplastin time of 50–70 seconds for 48 h with subsequent heparin administration left to the discretion of the treating physician. The first blood sample for activated partial thromboplastin time measurement was drawn after 3 h. Patients assigned enoxaparin co-therapy received an intravenous bolus of 30 mg immediately followed by the first subcutaneous dose of 1 mg/kg. To achieve sustained anticoagulation, this subcutaneous dose was repeated every 12 h up to hospital discharge or revascularization for a maximum of 7 days. The first two subcutaneous doses could not exceed 100 mg. Patients assigned abciximab co-therapy received a 0.25 mg/kg bolus and 0.125 µg/kg per min (maximum of 10 µg/min) for 12 h. Because abciximab has an anticoagulant effect, a lower dose of unfractionated heparin was given: 40 U/kg bolus (maximum of 3000 U) followed by 7 U/kg per h (maximum of 800 U/h) to achieve a partial thromboplastin time between 50 and 70 s. Also in this group, the first activated partial thromboplastin time was measured after 3 h. Aspirin (150–325 mg) was given to all patients. Intravenous boluses of unfractionated heparin, enoxaparin, and abciximab were to be given before bolus tenecteplase.

The primary endpoints were the composites of 30-day mortality, in-hospital reinfarction, or in-hospital refractory ischemia (primary efficacy endpoint) to evaluate efficacy outcomes, and the above plus in-hospital intracranial hemorrhage or in-hospital major bleeding other than intracranial bleeding (primary efficacy plus safety endpoint) to evaluate efficacy improvements when safety adverse events were added to the analysis.

Data were entered with the use of Oracle Clinical (version 3.1.1) and electronically transferred to the central database in Leuven, Belgium. Safety data were reported monthly to the data and safety monitoring committee. All stroke cases were reviewed by the same stroke committee that reviewed the stroke data in the ASSENT-2 trial. The members of this committee were unaware of treatment assignment. There was no central adjudication for the endpoints of reinfarction, refractory ischemia, and bleeding complications. However, definitions were provided to the investigators who, in addition, had to reconfirm the occurrence of these endpoints on a special form.

Reinfarction in the first 18 h was defined as recurrent symptoms of ischemia at rest accompanied by new or recurrent ST-segment elevations of 0.1 mV or more in at least two contiguous leads, lasting at least 30 min. After 18 h, the definition was: new Q waves in two or more leads, or further increases in concentrations of creatine kinase MB, troponins, or total creatine kinase above the upper limit of normal and increased over the previous value. Refractory ischemia was defined as symptoms of ischemia with ST-segment deviation or T-wave inversion persisting for at least 10 min despite medical management and not fulfilling the diagnosis of reinfarction. Non-cerebral bleeding complications were defined as major (requiring transfusion, intervention because of hemodynamic compromise, or both) or minor.

Statistical Analysis

Statistical analysis was by intention to treat. No confirmatory statistical hypothesis was prespecified, but a detailed analysis plan was defined before the database was locked. This analysis plan was based on generating risk ratios and CIs for the pairwise comparisons of primary interest. These comparisons were presented with the two-sided 95% CI of the relative risk and with nominal p values. For the primary endpoints, Kaplan-Meier curves were constructed and log-rank tests were done. For each endpoint, a two-sided 95% CI was also calculated and an overall X test, comparing the three treatment groups, was done. Comparisons of interest were prespecified to first involve the unfractionated heparin and enoxaparin groups. If these were not different, they were to be pooled and compared with the abciximab group. Otherwise, each experimental group was to be compared with the unfractionated heparin reference group.

On the basis of ASSENT-2, the estimated frequency of the primary efficacy endpoint in the group allocated full-dose tenecteplase and unfractionated heparin was 13.8%. The frequency of the primary efficacy plus safety endpoint in this group was 17.7%. On the basis of phase-II studies, it was assumed that the two experimental groups would result in a better, or at least similar, outcome when compared with standard treatment. The sample size and power calculations were therefore based on non-inferiority of the two experimental groups versus the reference group. The study had 80% power to exclude, with 95% confidence (one-sided), a 1% higher rate of the primary endpoints compared with the reference group, provided the point estimate in the experimental treatment group was 1.7% lower for the efficacy endpoint and 2.0% lower for the efficacy plus safety endpoint.

Figure 1:
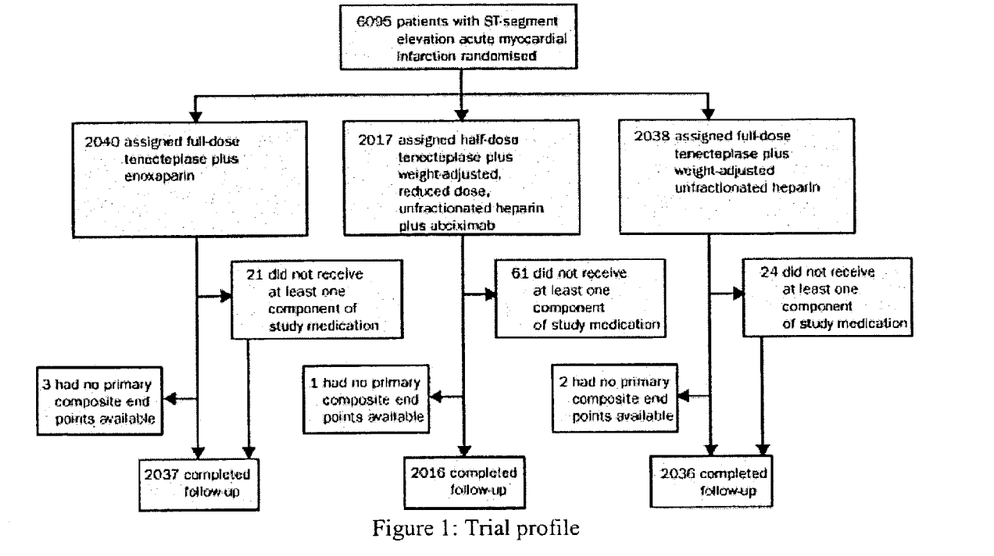
FIG. 1 shows the design of a randomized clinical trial (ASSENT-3) investigating the efficacy and safety of tenecteplase in combination with enoxaparin, abciximab, unfractionated heparin.

Results 6095 patients were enrolled between May, 2000, and April, 2001, of whom 5989 received study medication (FIG. 1). The baseline characteristics were similar in the three groups. Overall, the study populations were similar to those of previous trials on thrombolytics. The time from randomization to bolus tenecteplase was significantly longer in the abciximab group because of the complexity of the treatments and the need to give the boluses of heparin and abciximab before the tenecteplase bolus. Concomitant medications given in hospital included calcium-channel blockers, intravenous nitrates, β-blockers, ACE inhibitors, angiotensin II inhibitors, statins, aspirin, ticlopidin/clopidogrel, oral anticoagulants, Abciximab, other gpIIb/IIIa inhibitors, and thrombolytics, all conventionally used in cardiac treatment. High proportions of patients received β-blockers, angiotensin-converting-enzyme inhibitors, angiotensin-receptor blockers, statins, and thienopyridines. Abciximab and glycoprotein IIb/IIIa inhibitors other than study medication were given most frequently in the groups assigned full-dose tenecteplase and unfractionated heparin or enoxaparin. Likewise, low-molecular-weight heparins other than study medication were most frequently given to patients assigned unfractionated heparin or abciximab.

Figure 2:
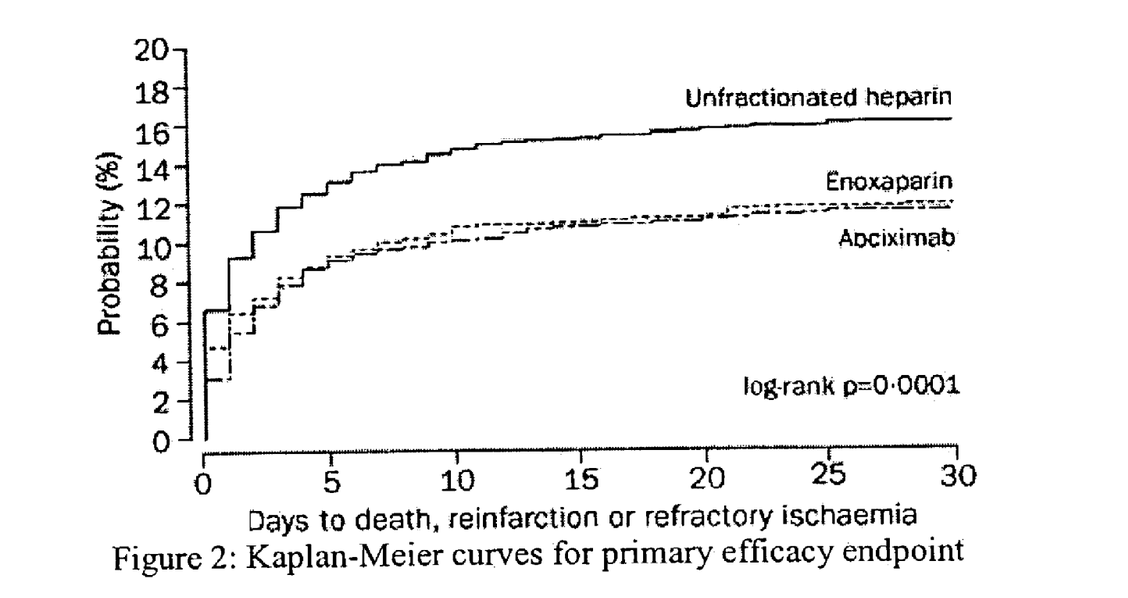
FIG. 2 shows the Kaplan-Meier curves for primary efficacy endpoint of ASSENT-3.
Figure 3:
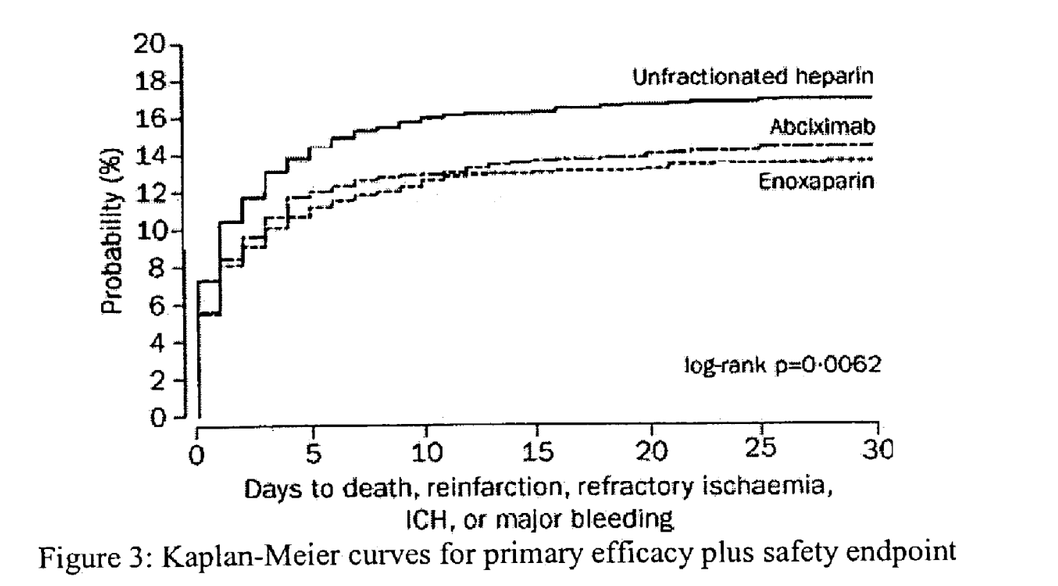
FIG. 3 shows the Kaplan-Meier curves for primary efficacy plus safety endpoint of ASSENT-3.

The primary efficacy and efficacy plus safety endpoints and their individual components in the three treatment groups are shown in Table 3. The combined efficacy and safety outcome in the full-dose tenecteplase plus unfractionated heparin group (Group III) of 17.0% was similar to that estimated (17.7%) before the trial commenced. The Kaplan-Meier curves for these primary endpoints are shown in FIGS. 2 and 3. Log-rank tests were highly significant. Early after treatment, the curves for the enoxaparin (Group I) and abciximab (Group II) groups started to separate from that of unfractionated heparin (Group III). At 48 h, the end of the unfractionated heparin infusion, differences in the primary endpoints among the three groups were already present. For the primary efficacy endpoint, event rates were 6.1% for full-dose tenecteplase plus enoxaparin, 5.2% for half-dose tenecteplase plus abciximab, and 8.8% for full-dose tenecteplase plus unfractionated heparin (p<0.0001). For the primary efficacy plus safety endpoint, the rates were 8.1, 8.2, and 10.3%, respectively (p=0.022).

TABLE 3

Frequency of composite and single endpoints at hospital discharge and at 30 days

| | Group I (n = 2040) | Group II (n = 2017) | Group III (n = 2038) | p |
|---|---|---|---|---|
| 30-day mortality, in-hospital reinfarction, or in-hospital refractory ischemia | 233/2037 (11.4%) | 223/2017 (11.1%) | 314/2038 (15.4%) | 0.0001 |
| 30-day mortality, in-hospital reinfarction, in-hospital refractory ischemia, in-hospital ICH, or in-hospital major bleeds (other than ICH) | 280/2037 (13.8) | 287/2016 (14.2%) | 347/2036 (17.0%) | 0.0081 |
| Death at 30 days | 109/2037 (5.4%) | 133/2017 (6.6%) | 122/2038 (6.0%) | 0.25 |
| In-hospital reinfarction | 54/2040 (2.7%) | 44/2017 (2.2%) | 86/2038 (4.2%) | 0.0009 |
| In-hospital refractory ischemia | 93/2040 (4.6%) | 64/2017 (3.2%) | 132/2038 (6.5%) | <0.0001 |
| In-hospital ICH | 18/2040 (0.9%) | 19/2017 (0.9%) | 19/2038 (0.9%) | 0.98 |
| Major bleeding (other than ICH) | 62/2040 (3.0%) | 87/2016 (4.3%) | 44/2035 (2/2%) | 0.0005 |

ICH = intracranial hemorrhage

Figure 4:
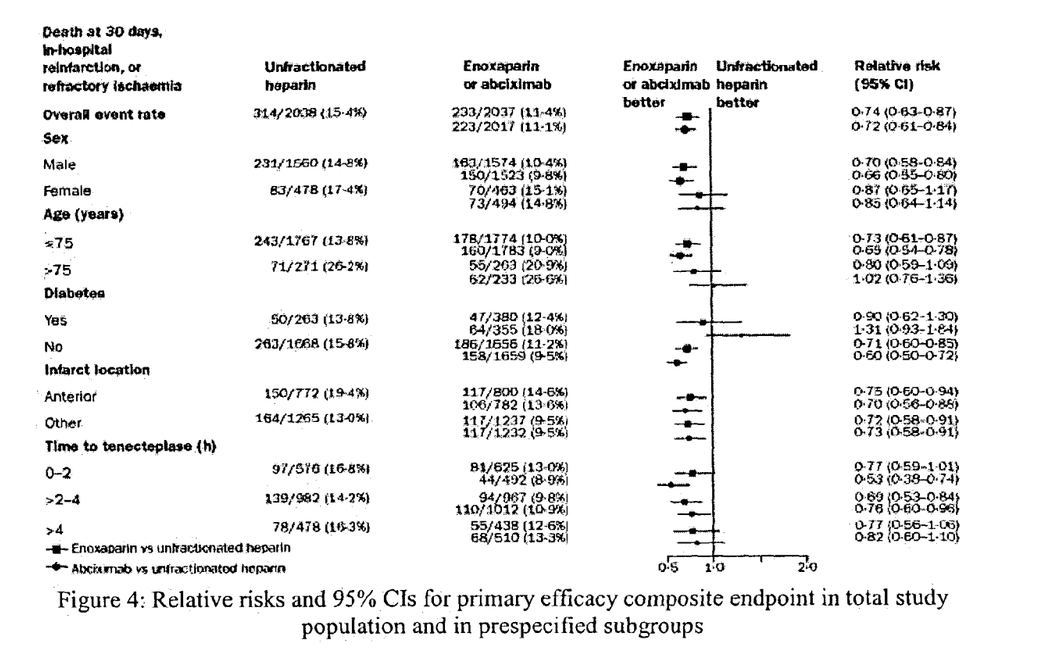
FIG. 4 shows the relative risks and 95% CIs for primary efficacy composite endpoint in the total ASSENT-3 study population and in prespecified subgroups.
Figure 5:
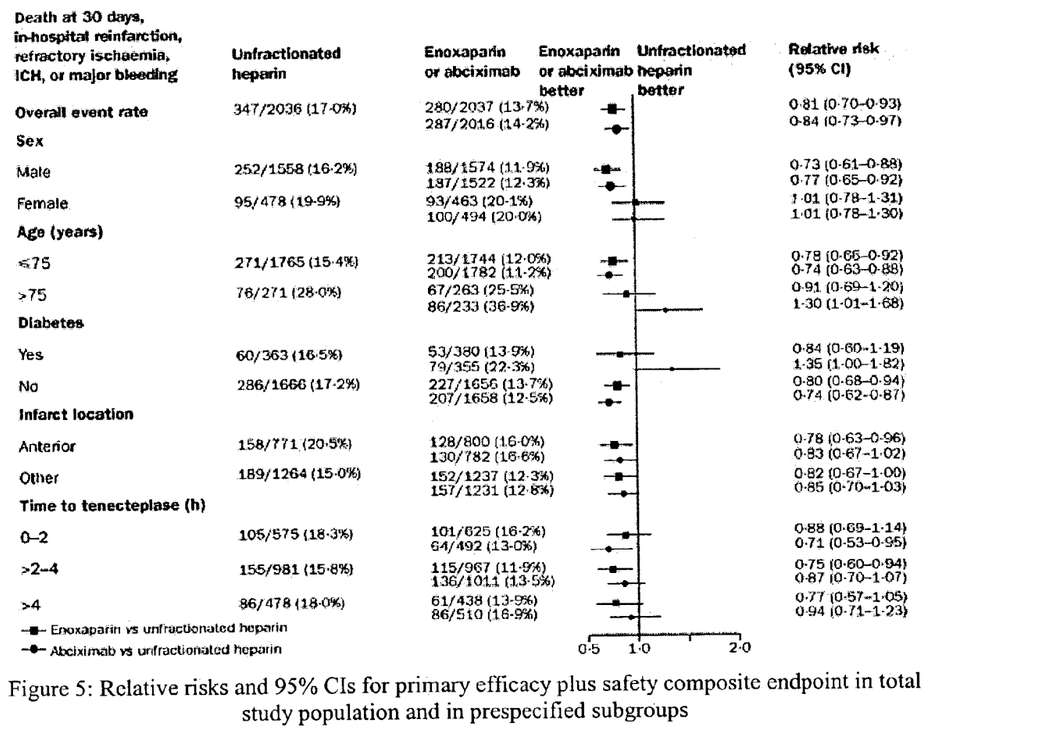
FIG. 5 shows the relative risks and 95% CIs for primary efficacy plus safety composite endpoint in the total ASSENT-3 study population and in prespecified subgroups.

The relative risks in the total population and in the prespecified subgroups are presented in FIGS. 4 and 5. The rates of the composite endpoints were lower among patients treated with enoxaparin or abciximab than among those treated with unfractionated heparin. Conventional statistical testing for full-dose tenecteplase plus enoxaparin versus full-dose tenecteplase plus unfractionated heparin resulted in p values of 0.0002 and 0.0037, respectively, for the primary efficacy and efficacy plus safety composite endpoints. The half-dose tenecteplase plus abciximab versus full-dose tenecteplase plus unfractionated heparin comparisons for the same primary endpoints yielded nominal p values of <0.0001 and 0.0142. After correcting for multiple testing (Bonferroni), conventional significance was reached for the primary efficacy endpoint in the abciximab group (p=0.0002) but not for the efficacy plus safety endpoint (p=0.057). For both the efficacy and efficacy plus safety endpoints, statistical significance was reached in the enoxaparin group (p=0.0009 and p=0.0146, respectively).

The lower point estimate of the relative risk of the composite endpoints was consistent across subgroups for the combination of full-dose tenecteplase and enoxaparin. For the combination of half-dose tenecteplase and abciximab, lower point estimates were seen in most subgroups, except in patients older than 75 years and those with diabetes (FIGS. 3 and 4). For the efficacy composite endpoint, the test for an interaction between treatment and diabetes was significant (p=0.0004). For the efficacy plus safety composite endpoint, the treatment interaction tests were significant for age (p=0.0010) and diabetes (p=0.0007). In women, lower point estimates of the relative risks of the efficacy composite endpoint were found in both experimental groups, whereas for the efficacy plus safety composite endpoint, the point estimates were on the line of unity.

No significant differences in 30-day mortality were present (Table 3). In-hospital reinfarction and refractory ischemia occurred less frequently in patients treated with enoxaparin or abciximab than in those treated with unfractionated heparin. The rates of in-hospital death or reinfarction were also lower in the enoxaparin and abciximab groups than in the unfractionated heparin group: 138/2040 (6.8%) and 148/2017 (7.3%) and 185/2038 (9.1%), respectively (p=0.0198). No significant reductions in other major cardiac complications were seen, with the exception of a significantly lower need for urgent percutaneous coronary interventions (ischemia-driven percutaneous coronary intervention before hospital discharge) in patients on enoxaparin or abciximab than in patients on unfractionated heparin. Total in-hospital stroke and intracranial hemorrhage rates were similar in the three groups.

Non-cerebral bleeding complications, need for transfusion, and rates of thrombocytopenia were also recorded. Significantly more major bleeding complications (p=0.0002), more transfusions (p=0.001), and a higher rate of thrombocytopenia (p=0.0001) were seen in the abciximab group (Group II) compared with the unfractionated heparin group (Group III). In patients older than 75 years and in diabetics, the rate of major bleeding complications was three times higher with abciximab than with unfractionated heparin: 11/271 (4.1%) versus 31/233 (13.3%), and 8/363 (2.2%) versus 25/355 (7.0%), respectively. More major bleeding complications and blood transfusions were also seen in the enoxaparin group (Group I) compared with unfractionated heparin, although these differences were not significant. There was no excess of thrombocytopenia in this treatment group. The total number of readmissions to hospital was similar in the three treatment groups: 254/1986 (12.8%) for enoxaparin, 221/1946 (11.4%) for abciximab, and 239/1984 (12.1%) for unfractionated heparin (p=0.39). A few additional strokes occurred after hospital discharge in the three groups. Total stroke rates and the rates of death or disabling stroke at 30 days remained similar: 39/2040 (1.9%) and 122/2037 (6.0%) for full-dose tenecteplase and enoxaparin, 37/2017 (1.8%) and 141/2016 (7.0%) for half-dose tenecteplase and abciximab, and 34/2038 (1.7%) and 132/2038 (6.5%) for full-dose tenecteplase and unfractionated heparin, respectively (p=0.83 for total stroke and p=0.43 for death or disabling stroke).

Discussion

The results of the group treated with full-dose tenecteplase and weight-adjusted unfractionated heparin (Group III) in this trial were very similar to those of ASSENT-2. In ASSENT-2, a higher and not fully weight-adjusted dose of unfractionated heparin was given and the first partial thromboplastin time was measured 6 h after start of treatment. Nonetheless, total mortality, reinfarction, total stroke, and intracranial hemorrhage rates were almost identical in both trials. However, there were fewer major bleeding complications (2.2% vs 4.7%) and less need for blood transfusion (2.3% vs 4.3%) in the present trial than in ASSENT-2. These results indirectly support the use of a more fully weight-adjusted dose of unfractionated heparin, as recommended in the ACC/AHA guidelines, together with earlier monitoring of the partial thromboplastin time. This unfractionated heparin dosing, however, was not associated with a reduction in the rate of intracranial hemorrhage, by contrast with the findings of a recent post-hoc analysis of the Intravenous tPA for the Treatment of Infarcting Myocardium Early (In-TIME)-II data. Guigliano et al., *Am. Heart J.* 141:742–50 (2001).

Compared with unfractionated heparin, adjunctive therapy with abciximab or enoxaparin reduces ischemic complications of acute myocardial infarction treated with tenecteplase. These reductions were found to be present early after the start of treatment. The results obtained with half-dose tenecteplase plus abciximab are very similar to those with half-dose reteplase and abciximab seen in GUSTO-V, and support the hypothesis that a more potent antiplatelet agent increases flow in the infarct-related coronary artery. In both trials, these benefits are obtained at the cost of a higher rate of thrombocytopenia, major bleeding complications, and blood transfusions. No benefit, and perhaps even harm, was seen in patients older than 75 years and in diabetics. By contrast with the present study, a 0.6% reduction in 30-day mortality was found in diabetic patients enrolled in GUSTO-V. Whether the findings in diabetics from the smaller ASSENT-3 study describd in this Example is due to chance or some other reason is unknown. Conversely, the data from both trials for this combination in elderly patients are consistent. Taken together, they suggest that caution should be exercised regarding the use of conjunctive therapy with abciximab in elderly patients with an acute myocardial infarction treated with a fibrinolytic agent. Further studies in the important and growing population of elderly patients with an acute myocardial infarction are warranted and might involve lower doses of these agents and mechanical approaches to reperfusion. The GUSTO-V and current results with half-dose fibrinolytic and abciximab suggest that there might be a role for this combination treatment in younger patients who are likely to undergo early coronary interventions. This speculation needs to be formally tested in future trials.

The reductions in ischemic complications in the full-dose tenecteplase plus enoxaparin group were similar to those seen in the abciximab group, but were more consistent. Importantly, no increase in intracranial hemorrhage rate, no excess in thrombocytopenia, and only a modest and non-significant increase in major bleeding complications was seen despite the length of treatment. In view of the present data and the ease of administration, enoxaparin is regarded as an attractive alternative anticoagulant treatment when given in combination with tenecteplase.

The overall 30-day mortality rates in the present study were low and probably result from selection of patients and an improvement in associated medical treatment and intervention. However, time to treatment remained similar to that of other large trials of fibrinolytic therapy, emphasizing the opportunity provided by prehospital therapy with simple regimens. This opportunity is currently being explored in the ASSENT-3 plus study which will compare the two full-dose tenecteplase cohorts administered out-of-hospital versus a matched population from the current study.

Like all clinical studies, the present study has some limitations. Ascertainment of selected components of the composite endpoints in this open trial was investigator-determined and subject to bias. The primary goal was to examine whether addition of a low-molecular-weight heparin or a platelet glycoprotein IIb/IIIa inhibitor to a fibrinolytic agent had promise as a therapeutic approach, and thus statistical hypotheses were not defined a priori. Nonetheless, the strength and consistency of the results suggest that they are not due to bias or chance. The observed treatment effects with both experimental groups exceeded what was expected in this intermediate-sized trial and raises the question as to whether our exploratory experimental approach will be useful in future assessments of promising combinations and various dosing regimens before large, definitive trials are done. The different duration of heparin therapy in the enoxaparin versus the unfractionated heparin group also deserves comment. We chose a 7-day course of enoxaparin to conform with previous studies in the hope of reducing recurrent ischemic complications and preventing reocclusion; the 48-h infusion of unfractionated heparin is a standard antithrombotic strategy used in previous trials such as ASSENT-2. The longer exposure to enoxaparin possibly contributed to its increased efficacy and to the increased trend for bleeding.

Taking into account efficacy and safety, the combination of full-dose tenecteplase and long-term administration of enoxaparin emerged as the best treatment, and the most promising reperfusion therapy regimen, in this trial. This easy-to-administer therapy regimen lowered event rates, and exhibited an improved safety profile. Because of additional advantages such as the ease of administration and the lack of need for monitoring of anticoagulation, this combination should be regarded as an attractive alternative pharmacological reperfusion strategy.

Summary

In summary, while both Groups I and Group II improved the efficacy of the composite endpoint compared to Group III, only the tenecteplase plus enoxaparin arm (Group I) maintained this benefit when safety adverse events were added to the analysis. Group I demonstrated the best results in reduction of events associated with the "primary efficacy plus safety" composite endpoint, including 30-day mortality, in-hospital reinfarction or in-hospital ischemia, and reduction in in-hospital ICH or major bleeding complications.

While Group II (tenecteplase plus unfractionated heparin plus abciximab) did demonstrate an improvement in efficacy over Group III, Group II was associated with an increase in major bleeding complications including non-cerebral bleeding, need for transfusions and the occurrence of thrombocytopenia, particularly in patients with diabetes or age 75 or older, compared to Group I and Group III. Thus, Group I showed the best results in the "efficacy plus safety" analysis, with an event rate of 13.75% compared with Group II (14.24%) and Group III (17.04%).

Generally similar across all three groups, the mortality rate, evaluated as part of the combined efficacy plus safety endpoint, was lowest in Group I, at 5.35%, compared to Group II at 6.59% and Group III at 5.99%. The differences were not statistically significant.

Although the present invention is illustrated with reference to certain embodiments, various modifications of the invention in addition to those shown and described herein will become apparent to those skilled in the art from the foregoing description and general knowledge in the art, and fall within the scope of the appended claims.

What is claimed is:

1. A method of increasing the efficacy and safety of thrombolytic therapy, comprising administering to a human patient 75 years of age or younger following myocardial infarction a therapeutically effective bodyweight adjusted single-bolus of a human tissue plasminogen activator (ht-PA) variant suitable for single-bolus administration, and a bodyweight adjusted dose of low molecular weight heparin without administration of unfractionated heparin, whereby the likelihood of 30-day survival of said patient is increased relative to treatment with said ht-PA variant and unfractionated heparin, without increase in the likelihood of a major bleeding incident.

2. The method of claim 1 wherein said ht-PA variant is glycosylated at any of positions 103–105, and devoid of functional carbohydrate structure at position 117 of wild-type ht-PA amino acid sequence, and exhibits a) extended circulatory half-life and fibrin-binding affinity within about two-fold of the wild-type ht-PA fibrin binding affinity or improved in vivo fibrinolytic potency, and b) improved fibrin specificity, as compared to wild-type ht-PA.

3. The method of claim 2 wherein said ht-PA variant has extended circulatory half-life and fibrin-binding affinity within about two-fold of the wild-type ht-PA fibrin binding affinity as compared to wild-type ht-PA.

4. The method of claim 2 wherein said ht-PA variant has improved in vivo fibrinolytic potency as compared to wild-type ht-PA.

5. The method of claim 2 wherein said ht-PA variant is glycosylated at position 103 of the wild-type ht-PA amino acid sequence.

6. The method of claim 5 wherein said glycosylation is N-linked.

7. The method of claim 6 wherein said ht-PA variant has asparagine as part of an Asn-X-Ser or Asn-X-Thr tripeptidyl sequence, wherein Asn is asparagine, Ser is serine, Thr is threonine, and X is any amino acid except proline, at position 103 of the wild-type ht-PA amino acid sequence.

8. The method of claim 7 wherein said ht-PA variant has asparagine at position 103, tryptophan at position 104, and serine at position 105 of the wild-type ht-PA amino acid sequence.

9. The method of claim 5 wherein said ht-PA variant has an amino acid other than asparagine at position 117 of the wild-type ht-PA amino acid sequence.

10. The method of claim 7 wherein said ht-PA variant has an amino acid other than asparagine at position 117 of the wild-type ht-PA amino acid sequence.

11. The method of claim 8 wherein said ht-PA variant has an amino acid other than asparagine at position 117 of the wild-type ht-PA amino acid sequence.

12. The method of claim 9 wherein said variant has improved fibrin specificity as compared to wild-type ht-PA.

13. The method of claim 12 wherein said improved fibrin specificity is achieved by an alteration within the amino acid region 296–302 or 274–277 of the wild-type ht-PA amino sequence.

14. The method of claim 13 wherein said alteration is in the region 296–299 of the wild-type ht-PA amino acid sequence.

15. The method of claim 14 wherein said alteration is the substitution of alanine for each of amino acids lysine, histidine, arginine, arginine at positions 296, 297, 298, and 299 of the wild-type ht-PA amino acid sequence.

16. The method of claim 1 wherein said low molecular weight heparin is selected from the group consisting of enoxaparin, dalteparin, tinzaparin, certoparin, parnaparin, nadroparin, ardeparin, and reviparin.

17. The method of claim 16 wherein said low molecular weight heparin is enoxaparin.

18. The method of claim 1 wherein said ht-PA variant is administered intravenously as a single bolus dose.

19. The method of claim 18 wherein said administration takes place within about 8 hours following the onset of symptoms requiring thrombolytic therapy.

20. The method of claim 18 wherein the bolus dose is weight adjusted.

21. The method of claim 20 wherein said bolus is administered within about 5 seconds.

22. The method of claim 21 wherein said ht-PA variant is tenecteplase.

23. The method of claim 22 wherein said bolus dose is about 30 mg for a patient having a bodyweight less than about 60 kg.

24. The method of claim 22 wherein said bolus dose is about 35 mg for a patient having a bodyweight of about 60 to 69 kg.

25. The method of claim 22 wherein said bolus dose is about 40 mg for a patient having a bodyweight of about 70 to 79 kg.

26. The method of claim 22 wherein said bolus dose is about 45 mg for a patient having a bodyweight of about 80 to 89 kg.

27. The method of claim 22 wherein said bolus dose is about 50 mg for a patient having a bodyweight of about 90 kg or more.

28. The method of claim 18 wherein administration of said low molecular weight heparin takes place before the single bolus administration of said ht-PA variant.

29. The method of claim 28 wherein said low molecular weight heparin is administered as an intravenous bolus followed by subcutaneous administration.

30. The method of claim 29 wherein said subcutaneous administration is repeated.

31. The method of claim 30 wherein said subcutaneous administration is repeated about every 12 hours for a maximum of about 7 days.

32. The method of claim 28 wherein said low molecule weight heparin is enoxapann.

33. The method of claim 32 wherein said enoxaparin is administered as an intravenous bolus of about 30 mg immediately followed by a subcutaneous dose of about 1 mg/kg.

34. The method of claim 33 wherein said subcutaneous dose is repeated about every 12 hours for a maximum of about 7 days.

35. The method of claim 1 wherein said patient is additionally administered aspirin.

36. The method of claim 1 wherein said patient is non-diabetic.

37. The method of claim 1 wherein said patient is monitored for at least 30 days.

38. The method of claim 37 wherein said patient does not suffer reinfarotion during the period of monitoring.

39. The method of claim 37 wherein said patient is not diagnosed with refractory ischemia during the period of monitoring.

40. The method of claim 37 wherein said patient does not suffer intracranial hemorrhage or other major bleeding during the period of monitoring.

* * * * *

UNITED STATES PATENT AND TRADEMARK OFFICE
CERTIFICATE OF CORRECTION

PATENT NO. : 7,084,118 B2  Page 1 of 1
APPLICATION NO. : 10/371778
DATED : August 1, 2006
INVENTOR(S) : Armstrong et al.

It is certified that error appears in the above-identified patent and that said Letters Patent is hereby corrected as shown below:

Col. 22, Claim 32, line 35, delete "exonapann" and replace with --enoxaparin--.

Signed and Sealed this

Twenty-eighth Day of April, 2009

JOHN DOLL
*Acting Director of the United States Patent and Trademark Office*